(12) United States Patent
Kim et al.

(10) Patent No.: US 11,178,910 B2
(45) Date of Patent: Nov. 23, 2021

(54) VAPORIZER AND AEROSOL GENERATION DEVICE INCLUDING SAME

(71) Applicant: KT&G CORPORATION, Daejeon (KR)

(72) Inventors: Tae Hun Kim, Yongin-si (KR); Hwan Ock Choe, Changwon-si (KR)

(73) Assignee: KT&G CORPORATION, Daejeon (KR)

( * ) Notice: Subject to any disclaimer, the term of this patent is extended or adjusted under 35 U.S.C. 154(b) by 0 days.

(21) Appl. No.: 16/611,991

(22) PCT Filed: May 9, 2018

(86) PCT No.: PCT/KR2018/005306
§ 371 (c)(1),
(2) Date: Nov. 8, 2019

(87) PCT Pub. No.: WO2018/208078
PCT Pub. Date: Nov. 15, 2018

(65) Prior Publication Data
US 2021/0127742 A1    May 6, 2021

(30) Foreign Application Priority Data

May 11, 2017   (KR) .................... 10-2017-0058786
Oct. 30, 2017  (KR) .................... 10-2017-0142578
May 3, 2018    (KR) .................... 10-2018-0051468

(51) Int. Cl.
*A24F 40/42*     (2020.01)
*A24F 40/485*    (2020.01)
(Continued)

(52) U.S. Cl.
CPC ............ *A24F 40/485* (2020.01); *A24F 40/40* (2020.01); *A24F 40/42* (2020.01); *A24F 40/44* (2020.01);
(Continued)

(58) Field of Classification Search
None
See application file for complete search history.

(56) References Cited

U.S. PATENT DOCUMENTS 5,388,594 A   2/1995   Counts et al.
5,408,574 A   4/1995   Deevi et al.
(Continued)

FOREIGN PATENT DOCUMENTS

CA   2778903 A1   5/2011
CN   1126425 A    7/1995
(Continued)

OTHER PUBLICATIONS

Communication dated Dec. 9, 2019 from the Korean Intellectual Property Office in KR Application No. 10-2018-0051469.
(Continued)

*Primary Examiner* — James Harvey
(74) *Attorney, Agent, or Firm* — Sughrue Mion, PLLC

(57) ABSTRACT

A vaporizer includes: a liquid storage for storing liquid composition; an upper cap portion coupled with the liquid storage and having a cavity for introducing the liquid composition of the liquid storage; a lower cap portion coupled with the upper cap portion to form an aerosol-generating space; a liquid delivery element positioned in the aerosol-generating space between the upper cap portion and the lower cap portion, and configured to absorb the liquid composition transferred from the liquid storage; a sealing portion having a coupling recess supporting at least one of end portions of the liquid delivery element, positioned between the upper cap portion and the lower cap portion, connected to the cavity, and configured to deliver the liquid composition from the liquid storage to the at least one of the end portions of the liquid delivery element; a heating element configured to heat the liquid delivery element to generate aerosol; and a leg portion extending from the upper
(Continued)

cap portion to the lower cap portion, contacting at least a portion of the liquid delivery element, and configured to block a coupled portion between the coupling recess of the sealing portion and the at least one of the end portions of the liquid delivery element to block a flow of the liquid composition from the sealing portion to the aerosol-generating space.

13 Claims, 7 Drawing Sheets

(51) Int. Cl.
*A24F 40/40* (2020.01)
*A24F 40/44* (2020.01)
*A24F 40/10* (2020.01)
*A24F 40/20* (2020.01)
*A24F 40/46* (2020.01)

(52) U.S. Cl.
CPC ............ *A24F 40/10* (2020.01); *A24F 40/20* (2020.01); *A24F 40/46* (2020.01)

(56) References Cited

U.S. PATENT DOCUMENTS

| | | | |
|---|---|---|---|
| 5,505,214 A | 4/1996 | Collins et al. | |
| 5,665,262 A | 9/1997 | Hajaligol et al. | |
| 5,723,228 A | 3/1998 | Okamoto | |
| 5,750,964 A | 5/1998 | Counts et al. | |
| 5,878,752 A | 3/1999 | Adams et al. | |
| 6,026,820 A | 2/2000 | Baggett, Jr. et al. | |
| 6,615,840 B1 | 9/2003 | Fournier et al. | |
| 6,803,550 B2 | 10/2004 | Sharpe et al. | |
| 7,082,825 B2 | 8/2006 | Aoshima et al. | |
| 7,682,571 B2 | 3/2010 | Kim et al. | |
| 8,558,147 B2 | 10/2013 | Greim et al. | |
| 8,602,037 B2 | 12/2013 | Inagaki | |
| 8,833,364 B2 | 9/2014 | Buchberger | |
| 9,165,484 B2 | 10/2015 | Choi | |
| 9,295,286 B2 | 3/2016 | Shin | |
| 9,405,148 B2 | 8/2016 | Chang et al. | |
| 9,420,829 B2 | 8/2016 | Thorens et al. | |
| 9,516,899 B2 | 12/2016 | Plojoux et al. | |
| 9,532,600 B2 | 1/2017 | Thorens et al. | |
| 9,713,345 B2 | 7/2017 | Farine et al. | |
| 9,844,234 B2 | 12/2017 | Thorens et al. | |
| 9,848,651 B2 | 12/2017 | Wu | |
| 9,854,845 B2 | 1/2018 | Plojoux et al. | |
| 10,070,667 B2 | 9/2018 | Lord et al. | |
| 10,104,909 B2 | 10/2018 | Han et al. | |
| 10,104,911 B2 | 10/2018 | Thorens et al. | |
| 10,136,673 B2 | 11/2018 | Mironov | |
| 10,143,232 B2 | 12/2018 | Talon | |
| 10,368,584 B2 | 8/2019 | Fernando et al. | |
| 10,390,564 B2 | 8/2019 | Fernando et al. | |
| 10,426,193 B2 | 10/2019 | Schennum et al. | |
| 10,548,350 B2 | 2/2020 | Greim et al. | |
| 10,701,973 B2 | 7/2020 | Lee | |
| 10,842,194 B2 | 11/2020 | Batista et al. | |
| 11,051,550 B2 | 7/2021 | Lin et al. | |
| 2003/0226837 A1 | 12/2003 | Blake et al. | |
| 2004/0089314 A1 | 5/2004 | Felter et al. | |
| 2004/0149737 A1 | 8/2004 | Sharpe et al. | |
| 2005/0142036 A1 | 6/2005 | Kim et al. | |
| 2006/0267614 A1 | 11/2006 | Lee et al. | |
| 2007/0007266 A1 | 1/2007 | Sasaki et al. | |
| 2007/0074734 A1 | 4/2007 | Braunshteyn et al. | |
| 2007/0246382 A1 | 10/2007 | He | |
| 2010/0313901 A1 | 12/2010 | Fernando et al. | |
| 2011/0226236 A1 | 9/2011 | Buchberger | |
| 2013/0014772 A1 | 1/2013 | Liu | |
| 2013/0228191 A1 | 9/2013 | Newton | |
| 2013/0255675 A1 | 10/2013 | Liu | |
| 2014/0069424 A1 | 3/2014 | Poston et al. | |
| 2014/0217085 A1 | 8/2014 | Alima | |
| 2014/0261487 A1 | 9/2014 | Chapman et al. | |
| 2014/0286630 A1 | 9/2014 | Buchberger | |
| 2014/0339509 A1 | 11/2014 | Choi et al. | |
| 2014/0345633 A1 | 11/2014 | Talon et al. | |
| 2015/0020831 A1 | 1/2015 | Weigenberg et al. | |
| 2015/0223520 A1 | 8/2015 | Phillips et al. | |
| 2015/0230521 A1 | 8/2015 | Talon | |
| 2015/0282527 A1 | 10/2015 | Henry, Jr. | |
| 2015/0327596 A1 | 11/2015 | Alarcon et al. | |
| 2016/0103364 A1 | 4/2016 | Nam et al. | |
| 2016/0128386 A1 | 5/2016 | Chen | |
| 2016/0174613 A1 | 6/2016 | Zuber et al. | |
| 2016/0205998 A1 | 7/2016 | Matsumoto et al. | |
| 2016/0321879 A1 | 11/2016 | Oh et al. | |
| 2016/0324216 A1 | 11/2016 | Li et al. | |
| 2016/0345625 A1 | 12/2016 | Liu | |
| 2017/0006915 A1* | 1/2017 | Li | A24F 40/42 |
| 2017/0042227 A1 | 2/2017 | Gavrielov et al. | |
| 2017/0055589 A1 | 3/2017 | Fernando et al. | |
| 2017/0064994 A1* | 3/2017 | Xu | B65D 25/08 |
| 2017/0064999 A1* | 3/2017 | Perez | B65D 25/04 |
| 2017/0119051 A1 | 5/2017 | Blandino et al. | |
| 2017/0143041 A1 | 5/2017 | Batista et al. | |
| 2017/0188634 A1 | 7/2017 | Plojoux et al. | |
| 2017/0197043 A1 | 7/2017 | Buchberger | |
| 2017/0197046 A1 | 7/2017 | Buchberger | |
| 2017/0214261 A1 | 7/2017 | Gratton | |
| 2017/0238609 A1 | 8/2017 | Schlipf | |
| 2017/0295844 A1 | 10/2017 | Thevenaz et al. | |
| 2017/0347715 A1 | 12/2017 | Mironov et al. | |
| 2018/0027878 A1 | 2/2018 | Dendy et al. | |
| 2018/0028993 A1 | 2/2018 | Dubief | |
| 2018/0160733 A1 | 6/2018 | Leadley et al. | |
| 2018/0199630 A1 | 7/2018 | Qiu | |
| 2019/0046745 A1* | 2/2019 | Nettenstrom | A61M 15/0021 |
| 2019/0059448 A1 | 2/2019 | Talon | |
| 2019/0159524 A1 | 5/2019 | Qiu | |
| 2019/0281896 A1 | 9/2019 | Chapman et al. | |
| 2020/0000144 A1 | 1/2020 | Schennum et al. | |
| 2020/0093185 A1 | 3/2020 | Lim | |
| 2020/0094997 A1 | 3/2020 | Menon et al. | |
| 2020/0154765 A1 | 5/2020 | Lee et al. | |
| 2020/0196670 A1 | 6/2020 | Alarcon et al. | |
| 2020/0260790 A1 | 8/2020 | Kaufman et al. | |
| 2020/0305240 A1 | 9/2020 | Holoubek et al. | |
| 2020/0359681 A1 | 11/2020 | Han et al. | |
| 2020/0404969 A1 | 12/2020 | Zuber et al. | |
| 2021/0127742 A1* | 5/2021 | Kim | A24F 40/40 |

FOREIGN PATENT DOCUMENTS

| | | |
|---|---|---|
| CN | 202907797 U | 5/2013 |
| CN | 204120226 U | 1/2015 |
| CN | 204146340 U | 2/2015 |
| CN | 204393344 U | 6/2015 |
| CN | 105188430 A | 12/2015 |
| CN | 205180371 U | 4/2016 |
| CN | 205358225 U | 7/2016 |
| CN | 205456064 U | 8/2016 |
| CN | 106136331 A | 11/2016 |
| CN | 106235419 A | 12/2016 |
| CN | 106418729 A | 2/2017 |
| CN | 106473232 A | 3/2017 |
| CN | 106723379 A | 5/2017 |
| CN | 206442590 U | 8/2017 |
| CN | 206443214 U | 8/2017 |
| CN | 107183789 A | 9/2017 |
| CN | 206547882 U | 10/2017 |
| CN | 108013512 A | 5/2018 |
| EA | 201290392 A1 | 10/2012 |
| EA | 201290240 A1 | 12/2012 |
| EA | 026076 B1 | 2/2017 |
| EP | 0 438 862 A2 | 7/1991 |
| EP | 0917831 A1 | 5/1999 |
| EP | 0 822 760 B1 | 6/2003 |
| EP | 1 947 965 A2 | 7/2008 |
| EP | 2 201 850 A1 | 6/2010 |

(56) References Cited

FOREIGN PATENT DOCUMENTS

| | | |
|---|---|---|
| EP | 2316286 A1 | 5/2011 |
| EP | 2327318 A1 | 6/2011 |
| EP | 2340729 A1 | 7/2011 |
| EP | 2 368 449 A1 | 9/2011 |
| EP | 2 677 273 A1 | 12/2013 |
| EP | 2 921 065 A1 | 9/2015 |
| EP | 3 257 386 B1 | 6/2019 |
| EP | 3 248 486 B1 | 8/2019 |
| EP | 3 569 076 A1 | 11/2019 |
| EP | 3 248 485 B1 | 4/2020 |
| EP | 3656229 A2 | 5/2020 |
| GB | 2514893 A | 12/2014 |
| JP | 62-15793 A | 1/1987 |
| JP | 6-73784 U | 10/1994 |
| JP | 7-184627 A | 7/1995 |
| JP | 9-75058 A | 3/1997 |
| JP | 9-161822 A | 6/1997 |
| JP | 9-228919 A | 9/1997 |
| JP | 2003-527127 A | 9/2003 |
| JP | 2004-212102 A | 7/2004 |
| JP | 2005-199913 A | 7/2005 |
| JP | 2006-292620 A | 10/2006 |
| JP | 3898118 B2 | 3/2007 |
| JP | 2007-101639 A | 4/2007 |
| JP | 2010-266425 A | 11/2010 |
| JP | 2013-509160 A | 3/2013 |
| JP | 2013-524835 A | 6/2013 |
| JP | 2014-216287 A | 11/2014 |
| JP | 2014-533513 A | 12/2014 |
| JP | 2015-13192 A | 1/2015 |
| JP | 2015-503916 A | 2/2015 |
| JP | 2015-504669 A | 2/2015 |
| JP | 2015-506170 A | 3/2015 |
| JP | 2015-528307 A | 9/2015 |
| JP | 2016-512033 A | 4/2016 |
| JP | 2016-521552 A | 7/2016 |
| JP | 2017-510270 A | 4/2017 |
| JP | 2017-511123 A | 4/2017 |
| JP | 2017-522876 A | 8/2017 |
| KR | 10-1999-0081973 A | 11/1999 |
| KR | 20-0203233 Y1 | 11/2000 |
| KR | 10-0304044 B1 | 11/2001 |
| KR | 10-2004-0084899 A | 10/2004 |
| KR | 10-2005-0065896 A | 6/2005 |
| KR | 10-0495099 B1 | 11/2005 |
| KR | 10-2006-0121638 A | 11/2006 |
| KR | 10-0782063 B1 | 12/2007 |
| KR | 10-1012472 B1 | 2/2011 |
| KR | 10-2011-0096548 A | 8/2011 |
| KR | 10-1062248 B1 | 9/2011 |
| KR | 2020110008931 U | 9/2011 |
| KR | 10-2012-0027029 A | 3/2012 |
| KR | 10-2012-0050568 A | 5/2012 |
| KR | 20-0460461 Y1 | 5/2012 |
| KR | 10-1174189 B1 | 8/2012 |
| KR | 10-2012-0101637 A | 9/2012 |
| KR | 10-2012-0102131 A | 9/2012 |
| KR | 10-2012-0104533 A | 9/2012 |
| KR | 10-2012-0115488 A | 10/2012 |
| KR | 20-2012-0007263 U | 10/2012 |
| KR | 20-2012-0008751 U | 12/2012 |
| KR | 10-2013-0031025 A | 3/2013 |
| KR | 10-1239080 B1 | 3/2013 |
| KR | 10-2013-0084789 A | 7/2013 |
| KR | 10-2013-0139276 A | 12/2013 |
| KR | 10-2013-0139298 A | 12/2013 |
| KR | 10-1338073 B1 | 12/2013 |
| KR | 10-2014-0116055 A | 10/2014 |
| KR | 10-2014-0116381 A | 10/2014 |
| KR | 10-2014-0118980 A | 10/2014 |
| KR | 10-2014-0119029 A | 10/2014 |
| KR | 10-2014-0135568 A | 11/2014 |
| KR | 10-1465846 B | 11/2014 |
| KR | 10-1480423 B1 | 1/2015 |
| KR | 10-1486294 B1 | 1/2015 |
| KR | 10-2015-0111021 A | 10/2015 |
| KR | 10-2016-0005323 A | 1/2016 |
| KR | 10-2016-0012154 A | 2/2016 |
| KR | 1020160031801 A | 3/2016 |
| KR | 10-2016-0052607 A | 5/2016 |
| KR | 10-1631286 B1 | 6/2016 |
| KR | 10-1635340 B1 | 6/2016 |
| KR | 10-2016-0082570 A | 7/2016 |
| KR | 10-2016-0086118 A | 7/2016 |
| KR | 10-2016-0088163 A | 7/2016 |
| KR | 10-1660214 B1 | 9/2016 |
| KR | 10-1677547 B1 | 11/2016 |
| KR | 10-1679163 B1 | 11/2016 |
| KR | 10-2017-0006282 A | 1/2017 |
| KR | 10-2017-0020807 A | 2/2017 |
| KR | 10-1733448 B1 | 5/2017 |
| KR | 10-2017-0067171 A | 6/2017 |
| KR | 10-2017-0083596 A | 7/2017 |
| KR | 10-2017-0117444 A | 10/2017 |
| KR | 10-2017-0118233 A | 10/2017 |
| KR | 10-2018-0125852 A | 11/2018 |
| KR | 10-2018-0129637 A | 12/2018 |
| KR | 10-2019-0016907 A | 2/2019 |
| RU | 2 132 629 C1 | 7/1999 |
| RU | 2551944 C1 | 6/2015 |
| RU | 2611487 C2 | 2/2017 |
| RU | 2617297 C2 | 4/2017 |
| RU | 2 619 735 C1 | 5/2017 |
| RU | 2015152134 A | 6/2017 |
| WO | 9527412 A1 | 10/1995 |
| WO | 98/23171 A1 | 6/1998 |
| WO | 2007039794 A2 | 4/2007 |
| WO | 2009/044716 A1 | 4/2009 |
| WO | 2010073122 A1 | 7/2010 |
| WO | 2011/050964 A1 | 5/2011 |
| WO | 2011/063970 A1 | 6/2011 |
| WO | 2013102609 A2 | 7/2013 |
| WO | 2014/195679 A2 | 12/2014 |
| WO | 2015035510 A1 | 3/2015 |
| WO | 2015/070402 A1 | 5/2015 |
| WO | 2015/082560 A1 | 6/2015 |
| WO | 2015/174657 A1 | 11/2015 |
| WO | 2015/177046 A1 | 11/2015 |
| WO | 2015/189388 A1 | 12/2015 |
| WO | 2016/009202 A1 | 1/2016 |
| WO | 2016012795 A1 | 1/2016 |
| WO | 2016/096337 A1 | 6/2016 |
| WO | 2016/111633 A1 | 7/2016 |
| WO | 2016/123738 A1 | 8/2016 |
| WO | 2016/127541 A1 | 8/2016 |
| WO | 2016120177 A1 | 8/2016 |
| WO | 2016138689 A1 | 9/2016 |
| WO | 2016/199065 A1 | 12/2016 |
| WO | 2016/199066 A1 | 12/2016 |
| WO | 2016/207407 A1 | 12/2016 |
| WO | 2017/001818 A1 | 1/2017 |
| WO | 2017/005471 A1 | 1/2017 |
| WO | 2017/029089 A1 | 2/2017 |
| WO | 2017/163046 A1 | 9/2017 |
| WO | 2017/182485 A1 | 10/2017 |
| WO | 2017/211600 A1 | 12/2017 |
| WO | 2018190606 A1 | 10/2018 |
| WO | 2018191766 A1 | 10/2018 |
| WO | 2019/015343 A1 | 1/2019 |

OTHER PUBLICATIONS

Communication dated Dec. 9, 2019 from the Korean Intellectual Property Office in KR Application No. 10-2018-0052133.
Communication dated Dec. 9, 2019 from the Korean Intellectual Property Office in KR Application No. 10-2018-0051467.
Extended European Search Report dated Jan. 15, 2021 in European Application No. 18799246.6.
Office Action dated May 25, 2020 in Russian Application No. 2019135871.
Office Action dated Jun. 10, 2020 in Korean Application No. 10-2018-0052137.

(56) References Cited

OTHER PUBLICATIONS

Office Action dated Oct. 5, 2020 in Korean Application No. 10-2020-0090577.
Office Action dated Oct. 16, 2020 in Korean Application No. 10-2020-0092553.
Extended European Search Report dated Nov. 16, 2020 in European Application No. 20189002.7.
Office Action dated Dec. 8, 2020 in Russian Application No. 2020113632.
Office Action dated Nov. 25, 2020 in Russian Application No. 2020124810.
Office Action dated Jan. 26, 2021 in Japanese Application No. 2020-502671.
Office Action dated Dec. 22, 2020 in Japanese Application No. 2020-502181.
Office Action dated Dec. 22, 2020 in Japanese Application No. 2020-503856.
Extended European Search Report dated Nov. 13, 2020 in European Application No. 20188970.6.
Office Action dated Nov. 10, 2020 in Japanese Application No. 2020-523671.
Office Action dated Nov. 24, 2020 in Russian Application No. 2020124811.
Communication dated Jul. 27, 2020 by the Russian Patent Office in application No. 2020110821.
Communication dated Jun. 11, 2020 by the Korean Patent Office in application No. 10-2018-0051469.
International Search Report dated Nov. 2, 2018 in International Application No. PCT/KR2018/005306.
International Search Report dated Aug. 28, 2018 in International Application No. PCT/KR2018/005693.
International Search Report dated Nov. 26, 2018 in International Application No. PCT/KR2018/005767.
International Search Report dated May 21, 2019 in International Application No. PCT/KR2018/012676.
International Search Report dated May 20, 2019 in International Application No. PCT/KR2018/012685.
International Search Report dated Apr. 3, 2019 in International Application No. PCT/KR2018/012773.
International Search Report dated Apr. 3, 2019 in International Application No. PCT/KR2018/012774.
International Search Report dated Apr. 3, 2019 in International Application No. PCT/KR2018/012775.
International Search Report dated May 17, 2019 in International Application No. PCT/KR2018/012776.
International Search Report dated May 3, 2019 in International Application No. PCT/KR2018/012807.
International Search Report dated May 17, 2019 in International Application No. PCT/KR2018/012808.
International Search Report dated May 17, 2019 in International Application No. PCT/KR2018/012809.
International Search Report dated May 17, 2019 in International Application No. PCT/KR2018/012810.
International Search Report dated Apr. 26, 2019 in International Application No. PCT/KR2018/012895.
International Search Report dated Apr. 16, 2019 in International Application No. PCT/KR2018/012899.
Office Action dated Feb. 9, 2018 in Korean Application No. 10-2017-0058786.
Office Action dated May 3, 2019 in Korean Application No. 10-2018-0055120.
Office Action dated May 13, 2019 in Korean Application No. 10-2018-0058596.
Office Action dated Jun. 19, 2019 in Korean Application No. 10-2018-0059580.
Office Action dated Jun. 24, 2019 in Korean Application No. 10-2018-0062137.
Office Action dated Jul. 10, 2019 in Korean Application No. 10-2018-0064487.
Office Action dated Sep. 6, 2019 in Korean Application No. 10-2018-0069645.
Office Action dated Oct. 8, 2019 in Korean Application No. 10-2018-0072935.
Office Action dated Oct. 8, 2019 in Korean Application No. 10-2018-0072992.
Office Action dated Oct. 15, 2019 in Korean Application No. 10-2018-0074188.
Office Action dated Oct. 25, 2019 in Korean Application No. 10-2018-0078296.
Office Action dated May 18, 2019 in Korean Application No. 10-2018-0090063.
Office Action dated Jul. 3, 2019 in Korean Application No. 10-2019-0016835.
Office Action dated Jul. 2, 2019 in Korean Application No. 10-2019-0017392.
Office Action dated Aug. 12, 2019 in Korean Application No. 10-2019-0033722.
Communication dated Feb. 24, 2021 by the Japanese Patent Office in application No. 2020-503962.
Communication dated Mar. 23, 2021 by the Japanese Patent Office in application No. 2020-522897.
Communication dated Mar. 2, 2021 by the Japanese Patent Office in application No. 2020-523669.
Communication dated Mar. 30, 2021 by the Japanese Patent Office in application No. 2020-501446.
Communication dated Mar. 16, 2021 by the Japanese Patent Office in application No. 2020-521441.
Communication dated Feb. 9, 2021 by the Japanese Patent Office in application No. 2020-501205.
Communication dated Mar. 16, 2021 by the European Patent Office in application No. 18806877.9.
Communication dated Apr. 5, 2019 by the Korean Patent Office in application No. 10-2019-0017393.
Communication dated Apr. 25, 2019 by the Korean Patent Office in application No. 10-2019-0033722.
Communication dated Apr. 25, 2019 by the Korean Patent Office in application No. 10-2019-0033723.
Communication dated Jun. 7, 2021 by the Canadian Patent Office in application No. 3,076,886.
Extended European Search Report dated Jul. 20, 2021 in European Application No. 18872006.4.
Notice of Reasons for Refusal dated Aug. 3, 2021 by the Japanese Patent Office in Japanese Application No. 2020-503856.
Extended European Search Report dated Aug. 6, 2021 in European Application No. 18872527.9.
Extended European Search Report dated Jul. 30, 2021 in European Application No. 18874446.0.
Communication dated Aug. 11, 2021, from the China National Intellectual Property Administration in application No. 201880029050.9.
Communication dated Sep. 2021, from the China National Intellectual Property Administration in application No. 201880035480.1.
Communication dated Sep. 2, 2021, from the European Patent Office in application No. 18874839.6.
Communication dated Aug. 20, 2021, from the European Patent Office in application No. 18874962.6.
Communication dated Aug. 12, 2021, from the European Patent office in application No. 18874837.0.
Communication dated Aug. 10, 2021, from the European Patent Office in application No. 18874742.2.
Communication dated Aug. 17, 2021, from the European Patent Office in application No. 18873943.7.
Communication dated Aug. 10, 2021, from the European Patent Office in application No. 18873846.2.
Communication dated Aug. 17, 2021, from the Japanese Patent Office in application No. 2020-503962.
Communication dated Aug. 17, 2021, from the European Patent office in application No. 18872432.2.
Communication dated Aug. 18, 2021, from the European Patent Office in application No. 18874344.7.

(56) References Cited

OTHER PUBLICATIONS

Communication dated Sep. 9, 2021, from the European Patent Office in application No. 18873562.5.

* cited by examiner

VAPORIZER AND AEROSOL GENERATION DEVICE INCLUDING SAME

CROSS REFERENCE TO RELATED APPLICATIONS

This application is a National Stage of International Application No. PCT/KR2018/005306 filed May 9, 2018, claiming priority based on Korean Patent Application No. 10-2017-0058786 filed May 11, 2017, Korean Patent Application No. 10-2017-0142578 filed Oct. 30, 2017 and Korean Patent Application No. 10-2018-0051468 filed May 3, 2018.

TECHNICAL FIELD

Exemplary embodiments relate to a vaporizer and an aerosol generation device including the same, and more particularly, to a vaporizer having a leakage prevention structure and an aerosol generation device including the same.

BACKGROUND ART

Recently, the demand for alternative methods to overcome the shortcomings of general cigarettes has increased. For example, there is an increasing demand for a method of generating aerosol by heating an aerosol-generating material in cigarettes, not a method of generating aerosol by combusting cigarettes. Accordingly, studies on a heating-type cigarette or a heating-type aerosol generation device have been actively conducted.

An aerosol generation device may include a vaporizer capable of producing aerosol. The vaporizer includes a liquid storage, and liquid composition included in the liquid storage is absorbed by a liquid delivery element and heated by a heating element. The heating element heats the liquid composition and external air to generate aerosol. Thus, the aerosol generation device has an airflow inlet that allows external air to enter the vaporizer.

When a user uses an aerosol generation device, the liquid composition flows from the liquid storage to the liquid delivery element. When the liquid composition flows, the path through which the liquid composition flows needs to be tightly sealed.

When the path through which the liquid composition flows is not tightly sealed, the liquid composition may leak into other components in the aerosol generation device or out of the aerosol generation device. The leaked liquid composition may flow out of the vaporizer and flow out to the airflow inlet of the aerosol generation device.

When the leakage of liquid occurs repeatedly, components of the aerosol generation device may be contaminated and the performance of the aerosol generation device may deteriorate, and the aerosol generation device may not operate. In addition, when the liquid composition is leaked to the airflow inlet of the aerosol generation device, the leaked liquid composition may make the user of the aerosol generation device feel unpleasant.

DESCRIPTION OF EXEMPLARY EMBODIMENTS

Technical Problem

Exemplary embodiments provide a vaporizer having a structure for preventing leakage of liquid composition and an aerosol generation device including the same.

Exemplary embodiments also provide an aerosol generation device having a water repellent coating to prevent the leakage of liquid into an airflow inlet.

Technical problems to be achieved by the present exemplary embodiments are not limited to the above-described technical problems, and other technical problems may be inferred from the following exemplary embodiments.

Solution to Problem

Exemplary embodiments provide a vaporizer including: a liquid storage for storing liquid composition; an upper cap portion coupled with the liquid storage and having a cavity for introducing the liquid composition of the liquid storage; a lower cap portion coupled with the upper cap portion to form an aerosol-generating space; a liquid delivery element positioned in the aerosol-generating space between the upper cap portion and the lower cap portion, and configured to absorb the liquid composition transferred from the liquid storage; a sealing portion having a coupling recess supporting at least one of end portions of the liquid delivery element, positioned between the upper cap portion and the lower cap portion, connected to the cavity, and configured to deliver the liquid composition from the liquid storage to the at least one of the end portions of the liquid delivery element; a heating element configured to heat the liquid delivery element to generate aerosol; and a leg portion extending from the upper cap portion to the lower cap portion, contacting at least a portion of the liquid delivery element, and configured to block a coupled portion between the coupling recess of the sealing portion and the at least one of the end portions of the liquid delivery element to block a flow of the liquid composition from the sealing portion to the aerosol-generating space.

A top end of the coupling recess facing the upper cap portion may be open.

The sealing portion may be coupled with the lower cap portion and positioned on facing sides of the lower cap portion to support each of the end portions of the liquid delivery element, extending from the facing sides of the lower cap portion to a center of the lower cap portion.

The liquid delivery element may be cylindrical, and the leg portion extends along at least a portion of an outer circumferential surface of the liquid delivery element, thereby surrounding the at least a portion of the outer circumferential surface of the liquid delivery element.

The coupling recess may surround the at least one of end portions of the liquid delivery element.

In another exemplary embodiment of the vaporizer, the sealing portion may further comprise an upper opening connected to the cavity, and a storage space for storing the liquid composition delivered from the upper opening and transferring, via connection to the coupling recess, the liquid composition to the at least one of end portions of the liquid delivery element inserted through the coupling recess.

The vaporizer may further include a liquid composition-absorbing member positioned between the liquid storage and the upper cap portion or between the upper cap portion and the sealing portion, and configured to delay the flow of the liquid composition absorbed by the liquid delivery element.

The upper cap portion, the lower cap portion, and the sealing portion may include an elastic material.

The heating element may have a coil- or filament-shape and may include at least one of nichrome, cantal, tantalum, stainless, tungsten, nickel and titanium.

The liquid delivery element may include at least one of cotton, silica wick, stainless steel mesh, and fiberglass.

Exemplary embodiments provide an aerosol generation device including: an airflow inlet; the vaporizer according to some exemplary embodiments in which aerosol is generated by heating external air introduced through the airflow inlet; and an air-flow path through which the aerosol is discharged.

The aerosol generation device may further include a water-repellent coating at the airflow inlet, wherein the water-repellent coating is processed to be water-repellent.

The water-repellent coating may have a mesh shape.

Advantageous Effects of Disclosure

A vaporizer according to exemplary embodiments has a structure for preventing the leakage of liquid. The structure for preventing the leakage of liquid may have an upper cap portion, a lower cap portion, and a sealing portion between the upper cap portion and the lower cap portion. Since the vaporizer has the structure for preventing the leakage of liquid, the path in an aerosol generation device, through which liquid composition flows, is tightly sealed and the flow of liquid is blocked from the outside to prevent the leakage of the liquid composition outside the flow path.

When the leakage of liquid to the outside of the vaporizer is prevented, problems that may occur in an aerosol generation device and to the user of the aerosol generation device by the leakage of the liquid composition, for example, the deterioration of the performance of the aerosol generation device and the malfunction of the aerosol generation device may be prevented.

The aerosol generation device according to an exemplary embodiment includes a water-repellent coating on an airflow inlet through which external air is introduced. The water-repellent coating allows external air to enter the aerosol generation device through the airflow inlet while preventing the liquid composition from being delivered to the user through the airflow inlet.

BEST MODE

Figure 1:
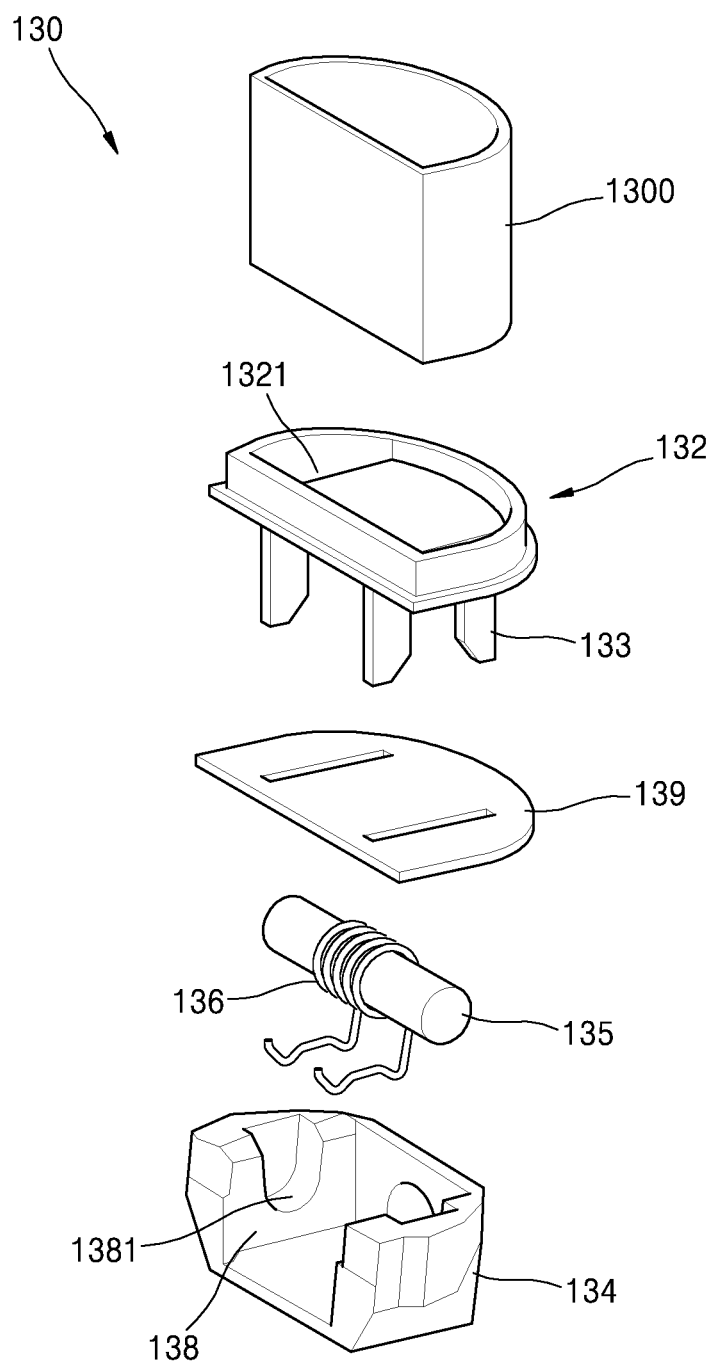
FIG. 1 is an exploded view of components of a vaporizer according to an exemplary embodiment.

A vaporizer according to an exemplary embodiment includes: a liquid storage for storing liquid composition; an upper cap portion coupled with the liquid storage and having a cavity through which the liquid composition of the liquid storage is introduced; a lower cap portion coupled with the upper cap portion to form an aerosol-generating space with the upper cap portion; a liquid delivery element positioned in the aerosol-generating space between the upper cap portion and the lower cap portion and absorbing the liquid composition transferred from the liquid storage; a sealing portion having a coupling recess supporting at least one of facing end portions of the liquid delivery element and positioned between the upper cap portion and the lower cap portion, and connected to the cavity to deliver the liquid composition from the liquid storage to at least one of the facing end portions of the liquid delivery element; a heating element for heating the liquid delivery element to generate aerosol; and a leg portion extending from the upper cap portion to the lower cap portion to contact at least a portion of the liquid delivery element and closing a coupled portion between the coupling recess of the sealing portion and the at least one of the facing end portions of the liquid delivery element to block a flow of the liquid composition from the sealing portion to the aerosol-generating space.

DETAILED DESCRIPTION OF EXEMPLARY EMBODIMENTS

With respect to the terms in the various exemplary embodiments, the general terms which are currently and widely used are selected in consideration of functions of structural elements in the various exemplary embodiments of the present disclosure. However, meanings of the terms may be changed according to intention, a judicial precedence, the appearance of a new technology, and the like. In addition, in certain cases, a term which is not commonly used may be selected. In such a case, the meaning of the term will be described in detail at the corresponding portion in the description of the present disclosure. Therefore, the terms used in the various exemplary embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and may be implemented by hardware components or software components and combinations thereof.

Hereinafter, example exemplary embodiments of the present disclosure will be described in detail with reference to the accompanying drawings. The disclosure can, however, be embodied in many different forms and should not be construed as limited to the exemplary embodiments set forth herein.

Hereinafter, exemplary embodiments of the present disclosure will be described in detail with reference to the drawings.

FIG. 1 shows an exploded view of components of a vaporizer 130 according to an exemplary embodiment. The vaporizer 130 includes a liquid storage 1300 for storing liquid composition, a liquid delivery element 135 for absorbing the liquid composition, and a heating element 136 for generating aerosol by heating the liquid delivery element 135.

In addition, the vaporizer 130 according to an exemplary embodiment has a leakage-prevention structure to prevent the leakage of liquid flowing out of the flow path in which the liquid composition flows from the liquid storage 1300 flows to the liquid delivery element 135. The leakage-prevention structure may include an upper cap portion 132 coupled with the liquid storage 1300, a lower cap portion 134 coupled with the upper cap portion 132 to form a space for generating aerosol, and a sealing portion 138 between the upper cap portion 132 and the lower cap portion 134.

The liquid storage 1300 may have a shape for storing liquid composition. The liquid storage 1300 may be, for example, in a prismatic shape including a cylindrical shape, or may be spherical. The liquid storage 1300 may also have an outlet to allow the liquid composition stored therein to flow out to the liquid delivery element 135. The liquid composition flows toward the upper cap portion 132 through the outlet of the liquid storage 1300.

The upper cap portion 132 may be coupled with the liquid storage 1300 to prevent the liquid composition flowing out of the outlet from leaking outside the vaporizer 130. The upper cap portion 132 may have a surface having such a shape that the upper cap portion 132 is tightly coupled with the liquid storage 1300. In order to be tightly coupled with the liquid storage 1300, the upper cap portion 132 may have a cap shape or a surface having a screw-thread shape.

The material for the upper cap portion 132 may be an elastic material, such as, for example, rubber or silicone. Since the upper cap portion 132 includes an elastic material, the upper cap portion 132 may provide tight sealing to the liquid storage 1300.

The upper cap portion 132 may have a cavity 1321 through which the liquid composition flowing from the liquid storage 1300 is introduced. The cavity 1321 may be formed in one surface of the upper cap portion 132, and may include a plurality of cavities. For example, the cavity 1321 may include two cavities which are formed at facing end portions of an upper surface of the upper cap portion 132. The cavity 1321 extends from one surface of the upper cap portion 132 toward the lower cap portion 134. The liquid composition flowing out of the liquid storage 1300 and toward the upper cap portion 132 may flow into an aerosol-generating space through the cavity 1321.

The lower cap portion 134 may have such a structure that the lower cap portion 134 is coupled to the upper cap portion 132 and form an aerosol-generating space between the upper cap portion 132 and the lower cap portion 134 by the coupling. The material for the lower cap portion 134 may be an elastic material, such as, for example, rubber or silicone. The aerosol-generating space may be a cavity which is formed inside when the upper cap portion 132 is coupled with the lower cap portion 134, and the liquid delivery element 135 may be positioned inside the aerosol-generating space.

The upper cap portion 132 and the lower cap portion 134 may each have a through portion through which external air may enter the aerosol-generating space. For example, the through portion may be a gap opened to an airflow path of the aerosol generation device 100 when the upper cap portion 132 is coupled with the lower cap portion 134. External air may enter the aerosol-generating space through the through portion. In addition, generated aerosol may flow out of the vaporizer 130 through the through portion and flow on the airflow path of an aerosol generation device. The through portion may be separated from a path on which the liquid composition flows.

The liquid delivery element 135 may be positioned in the aerosol-generating space formed between the upper cap portion 132 and the lower cap portion 134. The liquid delivery element 135 absorbs the liquid composition from the liquid storage 1300. The liquid delivery element 135 may include a material capable of absorbing the liquid composition which may be, for example, at least one of cotton, silica wick, stainless steel mesh, and glass fiber. The liquid delivery element 135 may have a prismatic shape having a cylindrical shape, but the shape of the liquid delivery element 135 is not limited thereto.

The sealing portion 138 for transferring the liquid composition introduced from the liquid storage 1300 through the upper cap portion 132 to the liquid delivery element 135 may be positioned between the upper cap portion 132 and the lower cap portion 134. The sealing portion 138 may be coupled with the upper cap portion 132 or the lower cap portion 134.

For example, the sealing portion 138 coupled with the lower cap portion 134 may be positioned on facing sides of the lower cap portion 134 and extend from the sides of the lower cap portion 134 toward the center of the lower cap portion 134. The sealing portion 138 may include a material having elasticity, such as, for example, rubber or silicone.

The sealing portion 138 may have a coupling recess 1381 supporting at least one of end portions of the liquid delivery element 135. The coupling recess 1381 may be provided to the sealing portion 138 on each of the facing sides of the lower cap portion 134. For example, when the liquid delivery element 135 is cylindrical, one end portion of the liquid delivery element 135 may be supported by one coupling recess 1381, and the other end portion of the liquid delivery element 135 may be supported by the other coupling recess 1381.

An upper end of the coupling recess 1381 facing the upper cap portion 132 may be open and a lower end thereof facing the lower cap portion 134 may be closed. The coupling recess 1381 may be formed to surround and support at least a portion of the outer circumferential surface of the end portion of the liquid delivery element 135.

The sealing portion 138 may be connected to the cavity 1321 of the upper cap portion 132 to transfer the liquid composition flowing from the liquid storage 1300 through the cavity 1321 to at least one of the end portions of the liquid delivery element 135. For example, the liquid composition flows out of the liquid storage and passes through the cavity 1321 of the upper cap portion 132 and the coupling recess 1381 of the sealing portion 138.

At least one of the end portions of the liquid delivery element 135 is supported by the coupling recess 1381, and the liquid delivery element 135 may include a material capable of absorbing the liquid composition. Accordingly, the liquid composition passing through the coupling recess 1381 may be absorbed by at least one of the end portions of the liquid delivery element 135, and as a result, the liquid composition is contained in the liquid delivery element 135.

The heating element 136 for generating aerosol by heating the liquid delivery element 135 may be formed to surround a portion of the liquid delivery element 135. For example, the heating element 136 may have the shape of a coil or a filament, and may be formed to surround the central portion of the liquid delivery element 135. The heating element 136 may include at least one of nichrome, cantal, tantalum, stainless, tungsten, nickel, and titanium.

When a user uses an aerosol generation device, the heating element 136 may be heated to a high temperature. The liquid composition contained in the liquid delivery element 135 and the external air introduced through the through portion may be heated and mixed by the heating element 136 in the aerosol-generating space to generate aerosol.

The upper cap portion 132 has leg portions 133 extending from the upper cap portion 132 toward the lower cap portion 134. When the upper cap portion 132 is coupled with the lower cap portion 134 to form the aerosol-generating space, the leg portions 133 may contact at least a portion of the liquid delivery element 135 of the sealing portion 138. In addition, the leg portions 133 may block the coupled portion of the coupling recess 1381 of the sealing portion 138 and at least one of the end portions of the liquid delivery element 135.

This will be described in detail in connection with FIG. 2, which shows a cross-section of the vaporizer 130 according to an exemplary embodiment.

The lower cap portion 134 has the coupling recess 1381 for supporting at least one of the end portions of the liquid delivery element 135, and the upper end of the coupling recess 1381 facing the upper cap portion 132 may be open. The remaining portion of the coupling recess 1381 may be formed to surround and support at least a portion of the outer circumferential surface of the end portion of the liquid delivery element 135.

The leg portion 133 may extend to the lower cap portion 134 along at least a portion of the outer circumferential surface of the liquid delivery element 135 to surround at least a portion of the outer circumferential surface of the liquid delivery element 135. The leg portion 133 and the sealing portion 138 may be in close contact with each other with respect to the length direction of the liquid delivery element 135. For example, a portion of the outer surface of the leg portion 133 may be in close contact with a portion of the inner surface of the sealing portion 138.

The coupled portion between the coupling recess 1381 of the sealing portion 138 and at least one of the end portions of the liquid delivery element 135 may be blocked by the leg portion 133. Accordingly, the flow of the liquid composition toward the aerosol-generating space through the coupling recess 1381 of the sealing portion 138 may be blocked, and the leakage of the liquid composition may be prevented. The liquid composition may be absorbed by the liquid delivery element 135 and moved to the aerosol-generating space via the liquid delivery element 135. The liquid composition may be heated and vaporized by the heating element 136.

The vaporizer 130 may further include a liquid composition-absorbing member 139, which is positioned between the liquid storage 1300 and the upper cap portion 132 or between the upper cap portion 132 and the sealing portion 138. The liquid composition-absorbing member 139 may delay the flow of the liquid composition absorbed by the liquid delivery element 135.

The liquid composition-absorbing member 139 absorbs the liquid composition flowing out of the liquid storage 1300 and then constantly discharges a predetermined amount thereof to prevent rapid flow of the liquid composition. For example, the liquid composition-absorbing member 139 may be positioned between the upper cap portion 132 and the sealing portion 138, and absorb the liquid composition flowing through the cavity 1321 of the upper cap portion 132 to the coupling recess 1381 of the sealing portion 138.

The liquid composition-absorbing member 139 may uniformly discharge a predetermined amount of the absorbed liquid composition to the coupling recess 1381 of the sealing portion 138 to prevent the leakage of liquid due to the rapid flow of the liquid composition. The liquid composition-absorbing member 139 has a material capable of constantly discharging a predetermined amount of the liquid composition after absorbing the liquid composition. Such a material may be, for example, fabric, felt or glass fiber.

Figure 2:
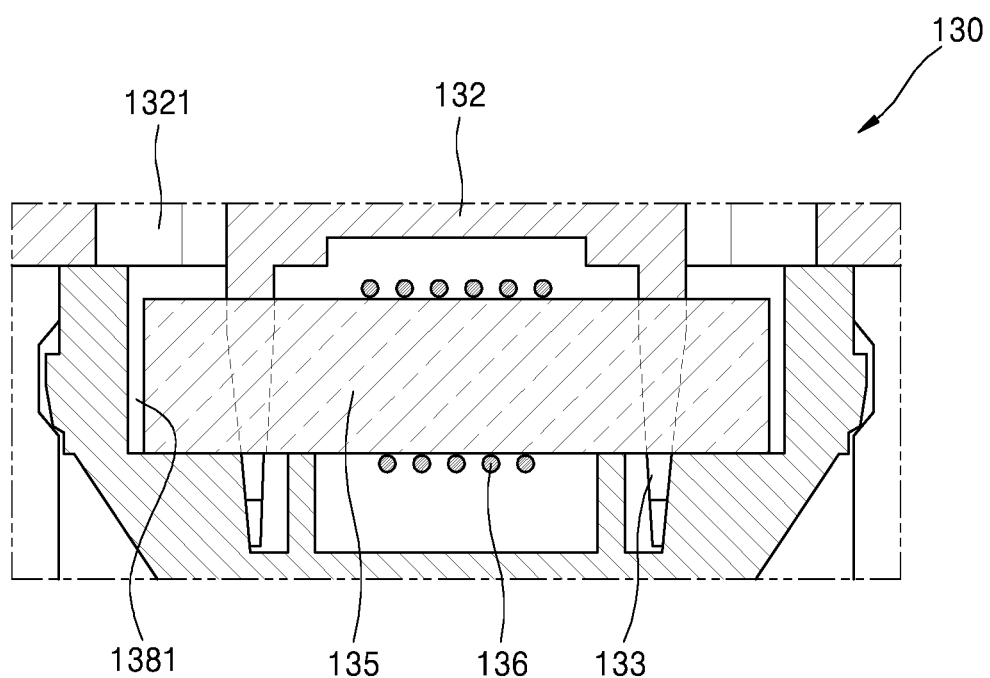
FIG. 2 is a cross-sectional view of the vaporizer according to the exemplary embodiment illustrated in FIG. 1.

Referring to the flow of the liquid composition in the vaporizer 130 of the exemplary embodiments illustrated in FIGS. 1 and 2, the liquid composition flowing out of the liquid storage 1300 may flow to the cavity 1321 of the upper cap portion 132. The liquid composition passing through the cavity 1321 of the upper cap portion 132 may flow directly into the coupling recess 1381 of the sealing portion 138 or may be absorbed by the liquid composition-absorbing member 139 and then flow into the coupling recess 1381 of the sealing portion 138 by a predetermined amount.

The coupled portion between the coupling recess 1381 of the sealing portion 138 and at least one of the end portions of the liquid delivery element 135 may be blocked by the leg portion 133. The flow of the liquid composition from the sealing portion 138 to the aerosol-generating space is blocked. The liquid composition may be absorbed by the liquid delivery element 135 and directed to the aerosol-generating space.

The liquid composition absorbed in the liquid delivery element 135 may be heated and vaporized while being contained in the liquid delivery element 135 by the heating element 136 which heats the liquid delivery element 135. External air enters the aerosol-generating space through the through portion of the vaporizer 130 to generate aerosol with the vaporized liquid composition.

The generated aerosol may flow along the airflow path of the aerosol generation device 100 through the through portion. The aerosol flowing along the airflow path may be delivered to the user through the cigarette.

Figure 3:
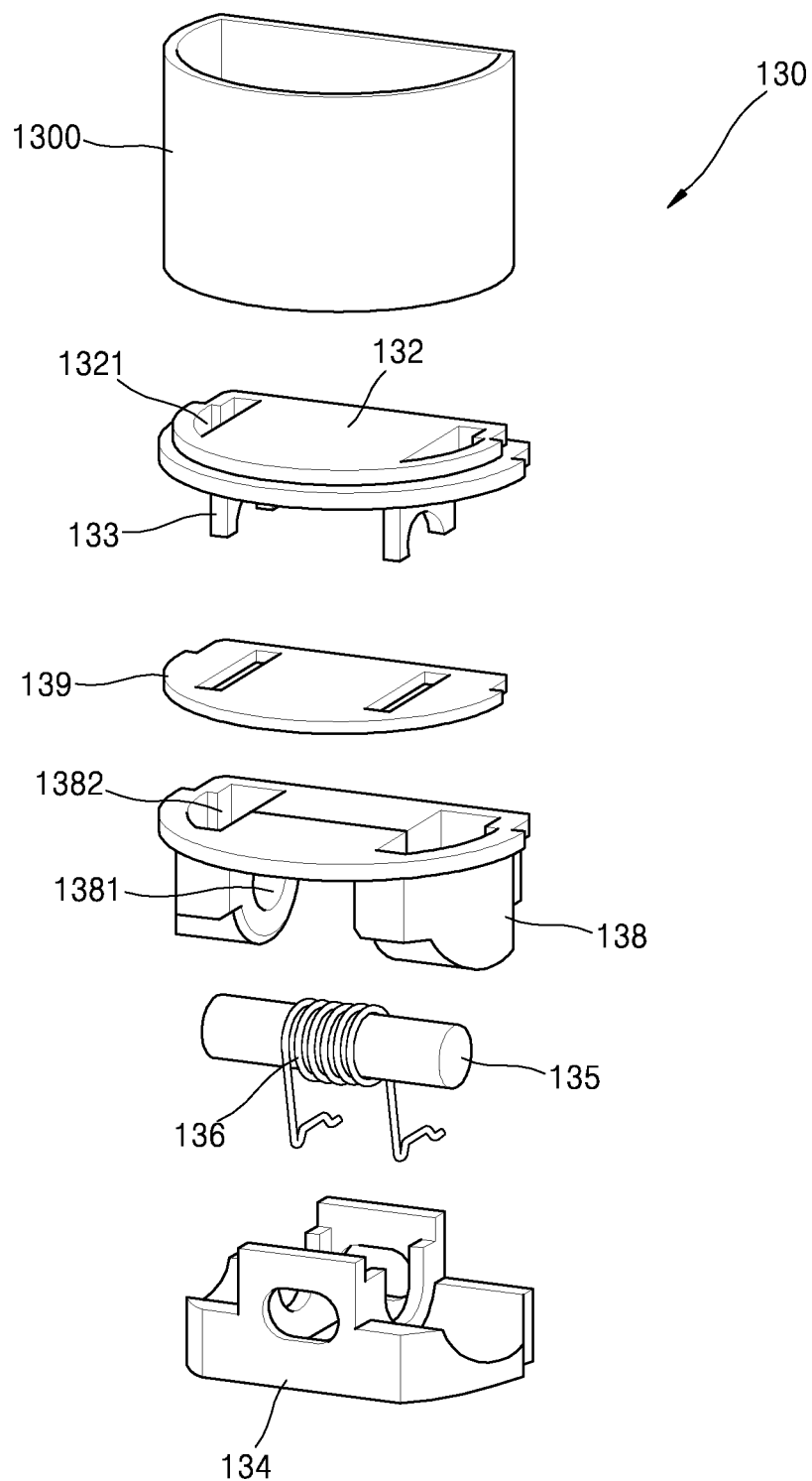
FIG. 3 is an exploded view of components of a vaporizer according to another exemplary embodiment.

FIG. 3 is an exploded view of components of a vaporizer 130 according to another exemplary embodiment. Detailed descriptions of the vaporizer 130 according to another exemplary embodiment shown in FIG. 3 is omitted as long as the descriptions are the same as the description of the vaporizer 130 provided in connection with the exemplary embodiments illustrated in FIGS. 1 and 2.

Referring to FIG. 3, the sealing portion 138 may transfer the liquid composition introduced from the liquid storage 1300 through the upper cap portion 132 to the liquid delivery element 135. The sealing portion 138 is positioned between the upper cap portion 132 and the lower cap portion 134.

The sealing portion 138 may comprise the coupling recess 1381 supporting at least one of end portions of the liquid delivery element 135. The coupling recess 1381 may have such a shape that the coupling recess 1381 surrounds at least one of the end portions of the liquid delivery element 135. For example, when the liquid delivery element 135 is cylindrical, the coupling recess 1381 may be circular to surround an end portion of the liquid delivery element 135.

The sealing portion 138 may be positioned between the upper cap portion 132 and the lower cap portion 134, and may be detachable from the upper cap portion 132 and the lower cap portion 134. The sealing portion 138 may have end portions protruding in the direction from the upper cap portion 132 toward the lower cap portion 134.

The sealing portion 138 may have an upper opening 1382 connected to the cavity 1321 of the upper cap portion 132. For example, the upper opening 1382 may be open to the upper cap portion 132 such that the liquid composition passing through the cavity 1321 of the upper cap portion 132 may flow to the upper opening 1382.

The liquid delivery element 135 may be positioned in the aerosol-generating space between the upper cap portion 132 and the lower cap portion 134 while at least one of the end portions of the liquid delivery element 135 is surrounded by the coupling recess 1381 of the sealing portion 138. The liquid delivery element 135 positioned in the aerosol-generating space may absorb the liquid composition, and the absorbed liquid composition may be heated by the heating element 136.

The heating element 136 for generating aerosol by heating the liquid delivery element 135 may be formed to surround a portion of the liquid delivery element 135. For example, the heating element 136 may have a coil shape or a filament shape, and may be formed to surround the central portion of the liquid delivery element 135.

Figure 4:
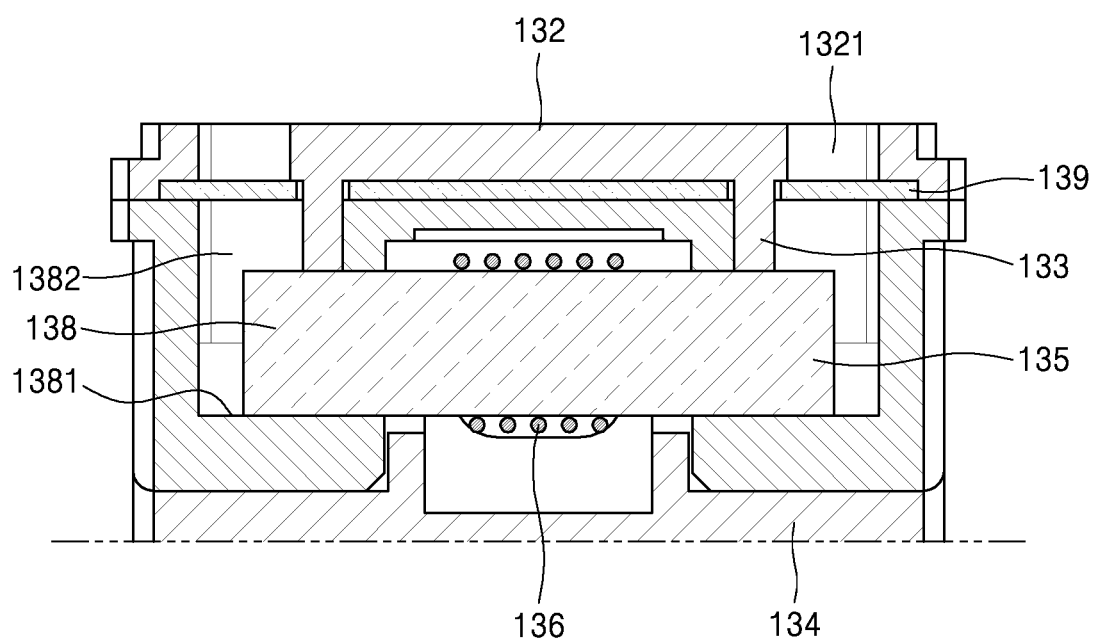
FIG. 4 is a cross-sectional view of the vaporizer according to the exemplary embodiment illustrated in FIG. 3.

Referring to FIG. 4, which shows the exemplary embodiment in which the respective components of the vaporizer 130 shown in FIG. 3 are assembled, the sealing portion 138 includes a storage space for storing liquid composition delivered from the cavity 1321 of the upper cap portion 132 through the upper opening 1382 of the sealing portion 138 connected to the cavity 1321.

The storage space is connected to the coupling recess 1381, and provides the liquid composition to at least one of end portions of the liquid delivery element 135 inserted through the coupling recess 1381. For example, the storage space may be a certain space between the upper opening 1382 of the sealing portion 138 and the coupling recess. The liquid composition, which has passed the upper opening 1382, may stay in the storage space before passing the coupling recess 1381.

The liquid composition flowing from the liquid storage 1300 may be stored in the storage space of the sealing portion 138 through the cavity 1321 of the upper cap portion 132 and the upper opening 1382 of the sealing portion 138. The storage space is connected to the coupling recess 1381, and the coupling recess 1381 may have such a shape that the coupling recess 1381 surrounds the end portion of the liquid delivery element 135.

The coupling recess 1381 may surround the end portion of liquid delivery element 135 and blocks the flow of the liquid composition from the storage space to the aerosol-generating space through the coupling recess 1381. The flow of the liquid composition to the aerosol-generating space is interrupted to prevent leakage of the liquid composition.

The vaporizer 130 may further include the liquid composition-absorbing member 139, which is positioned between the liquid storage 1300 and the upper cap portion 132 or between the upper cap portion 132 and the sealing portion 138. The liquid composition-absorbing member 139 may delay the flow of the liquid composition absorbed by the liquid delivery element 135.

The liquid composition-absorbing member 139 absorbs the liquid composition flowing out of the liquid storage 1300 and then constantly discharges a predetermined amount thereof to prevent rapid flow of the liquid composition. For example, the liquid composition-absorbing member 139 may be positioned between the upper cap portion 132 and the sealing portion 138 and absorb the liquid composition flowing to the upper opening 1382 of the sealing portion 138 and the storage space through the cavity 1321 of the upper cap portion 132.

The liquid composition-absorbing member 139 may uniformly discharge a predetermined amount of the absorbed liquid composition into the storage space of the sealing portion 138 to prevent excessive leakage of the liquid composition flowing to the storage space. Therefore, leakage of liquid through the coupling recess 1381 in the storage space of the sealing portion 138 may be prevented. The liquid composition-absorbing member 139 may have a material capable of constantly discharging a predetermined amount of the liquid composition after absorbing the liquid composition. Such a material may be, for example, fabric, felt or glass fiber.

Figure 5A:
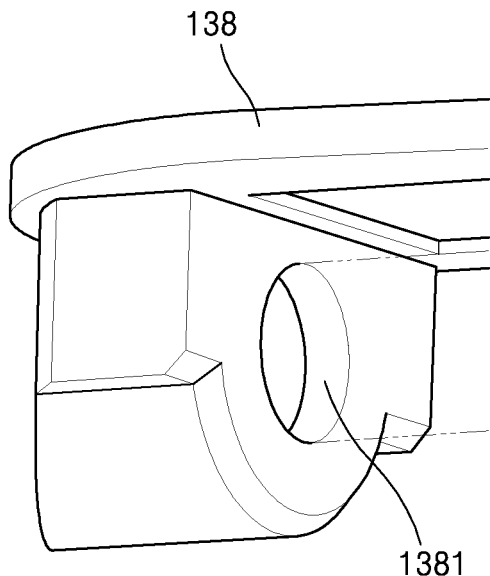
FIG. 5A is a perspective view of a coupling recess of a sealing portion among components of the vaporizer according to the exemplary embodiment illustrated in FIG. 3.

FIG. 5A illustrates the coupling recess 1381 of the sealing portion 138 from among the components of the vaporizer 130 according to the exemplary embodiment illustrated in FIG. 3. The sealing portion 138 may have, on both sides thereof, end portions protruding in the direction from the upper cap portion 132 to the lower cap portion 134, and the coupling recess 1381 may be formed in the inner surface of each of the protruding end portions.

The coupling recess 1381 of the sealing portion 138 may support at least one of the end portions of the liquid delivery element 135. The coupling recess 1381 may have a shape surrounding at least one of both end portions of the liquid delivery element 135. For example, the liquid delivery element 135 may be cylindrical, and the coupling recess may have a circular shape surrounding the end portion of the liquid delivery element 135. The end portion of the liquid delivery element 135 may fit into the coupling recess 1381 such that the flow of the liquid composition through the coupling recess 1381 without passing through the liquid delivery element 135 may be blocked.

Figure 5B:
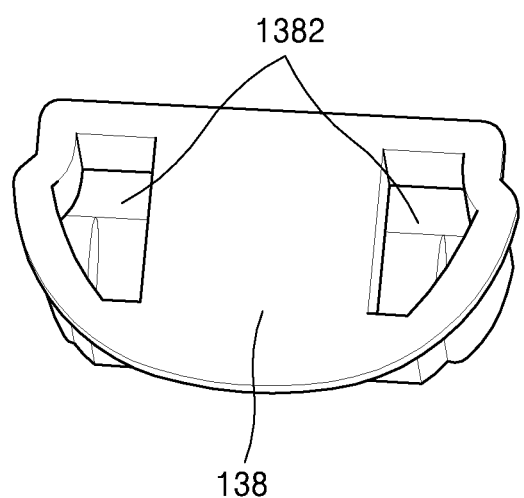
FIG. 5B is a plan view of upper openings of the sealing portion among components of the vaporizer according to the exemplary embodiment illustrated in FIG. 3.

FIG. 5B shows a plan view illustrating the upper opening 1382 of the sealing portion 138 from among the components of the vaporizer 130 according to the exemplary embodiment illustrated in FIG. 3. The sealing portion 138 may have the upper opening 1382 connected to the cavity 1321 of the upper cap portion 132. The upper opening 1382 may be open to the upper cap portion 132 such that the liquid composition passing through the cavity 1321 of the upper cap portion 132 may flow to the upper opening 1382.

The shape of the upper opening 1382 is not limited to a particular shape, and the upper opening 1382 is connected to a storage space for storing the liquid composition. The liquid composition that has passed through the upper opening 1382 may flow into the storage space inside the sealing portion 138 and stay in the storage space.

Referring to the flow of the liquid composition in the vaporizer 130 of the exemplary embodiments illustrated in FIGS. 3 and 4, the liquid composition flowing out of the liquid storage 1300 may flow to the cavity 1321 of the upper cap portion 132. The liquid composition passing through the cavity 1321 of the upper cap portion 132 may flow directly into the upper opening 1382 of the sealing portion 138 connected to the cavity 1321, or may be absorbed by the liquid composition-absorbing member 139 and then flow in a predetermined amount to the upper opening 1382 of the sealing portion 138.

The liquid composition that has passed through the upper opening 1382 may be stored and stay in the storage space of the sealing portion 138. The coupling recess 1381 supports the end portion of the liquid delivery element 135 while closely wrapping the end portion of the liquid delivery element 135. The flow of the liquid composition from the storage space to the aerosol-generating space through the coupling recess 1381 without passing through the liquid delivery element 135 is blocked, and the liquid composition is absorbed by the liquid delivery element 135 and flows to the aerosol-generating space through the liquid delivery element 135.

The liquid composition absorbed in the liquid delivery element 135 is heated and vaporized by the heating element 136, which heats the liquid delivery element 135 while the liquid composition is absorbed in the liquid delivery element 135. External air enters the aerosol-generating space through the through portion of the vaporizer 130 to generate aerosol together with the vaporized liquid composition.

The generated aerosol may flow along the airflow path of the aerosol generation device through the through portion. The aerosol flowing along the airflow path may be delivered to the user through the cigarette.

Figure 6:
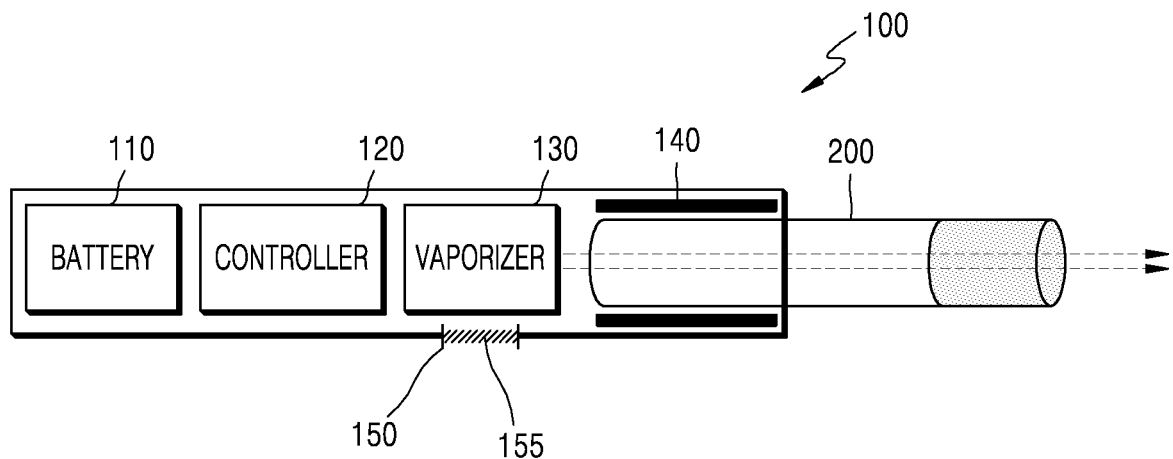
FIGS. 6 and 7 illustrate examples in which a cigarette is inserted into an aerosol generation device according to an exemplary embodiment.
Figure 7:
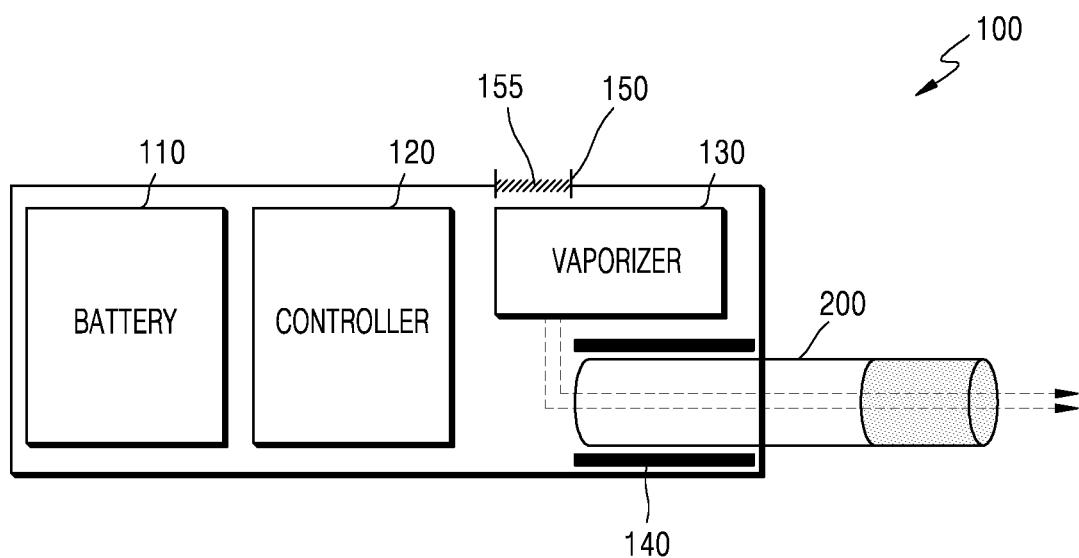

FIGS. 6 and 7 illustrate examples in which a cigarette is inserted into an aerosol generation device including a vaporizer according to an exemplary embodiment.

Referring to FIGS. 6 and 7, an aerosol generation device 100 includes a battery 110, a controller 120, a heater 140, and a vaporizer 130. In addition, a cigarette 200 may be inserted into the internal space of the aerosol generation device 100.

A person skilled in the art would understand that other general elements may be further included in the aerosol generation device 100 in addition to the elements illustrated in FIGS. 6 and 7.

FIGS. 6 and 7 illustrate that the heater 140 is provided in the aerosol generation device 100. However, the heater 140 may be omitted as necessary.

In FIG. 6, the battery 110, the controller 120, the vaporizer 130, and the heater 140 are arranged in a line. On the other hand, FIG. 7 shows that the vaporizer 130 and the heater 140 are arranged in parallel. However, the internal structure of the aerosol generation device 100 is not limited to those illustrated in FIGS. 6 and 7. In other words, according to the design of the aerosol generation device 100, the configuration of the battery 110, the controller 120, the vaporizer 130, and the heater 140 may be changed.

When the cigarette 200 is inserted into the aerosol generation device 100, the aerosol generation device 100 may operate the vaporizer 130 to generate aerosol from the vaporizer 130. The aerosol generated by the vaporizer 130 is delivered to the user through the cigarette 200.

The battery 110 supplies electric power used to operate the aerosol generation device 100. For example, the battery 110 may supply power for heating the heater 140 or the vaporizer 130 and may supply power for operating the controller 120. Furthermore, the battery 110 may supply power for operating a display, a sensor, or a motor which may be installed in the aerosol generation device 100.

The controller 120 controls the operation of the aerosol generation device 100. In detail, the controller 120 controls operations of other components in addition to the battery 110, the heater 140, and the vaporizer 130 included in the aerosol-generating device 100. The controller 120 may identify the state of each element of the aerosol generation device 100 to determine whether the aerosol generation device 100 is in an operable state.

The controller 120 may include at least one processor. A processor may be implemented as an array of a plurality of logic gates or may be implemented as a combination of a general purpose microprocessor and a memory in which a program executable in the microprocessor is stored. It will be understood by one of ordinary skill in the art that the processor may be implemented in other forms of hardware.

The heater 140 may be heated by the power supplied from the battery 110. For example, when the cigarette is inserted into the aerosol generation device 100, the heater 140 may be located around the cigarette. Thus, when heated, the heater 140 may raise the temperature of an aerosol-generating material in the cigarette.

The heater 140 may include an electrically resistive heater. For example, the heater 140 may include an electrically conductive track, and as the current flows in the electrically conductive track, the heater 140 may be heated. However, the heater 140 is not limited to the above-described example and may be applied without limitation as long as the heater 140 is able to be heated to a target temperature. Here, the target temperature may be set in the aerosol generation device 100 in advance or may be set to a desired temperature by the user.

Meanwhile, as another example, the heater 140 may be an induction-heating heater. In detail, the heater 140 may include an electrically conductive coil for heating the cigarette in an induction heating method, and the cigarette may include a susceptor that may be heated by an induction heating heater.

The aerosol generation device 100 may further include an airflow inlet 150 to allow external air to be introduced into the aerosol generation device 100. The airflow inlet 150 may be formed in one surface of the aerosol generation device 100. The external air may enter the aerosol generation device 100 through the airflow inlet 150 and may move to at least one of the components in the aerosol generation device 100.

For example, the external air may enter the aerosol generation device 100 through the airflow inlet 150 and move to the vaporizer 130. The external air moved to the vaporizer 130 may form an aerosol with the vaporized liquid composition.

In addition, the aerosol generation device 100 may further include a water-repellent coating 155 that is processed to be water-repellent at the airflow inlet 150. The water-repellent coating 155 is positioned at the airflow inlet 150 to prevent the leakage of the liquid composition through the airflow inlet 150 and at the same time to allow external air to enter the aerosol generation device 100 through the airflow inlet 150.

The shape of the water-repellent coating 155 may be like a net or a mesh but may be manufactured in various shapes without any limitation on the shape. The amount of external air introduced into the aerosol generation device 100 may be controlled according to the shape of a water-repellent coating. By controlling the amount of external air introduced into the aerosol generation device 100, the vaporizer 130 may generate high-quality aerosol.

The material for the water-repellent coating 155 may be a metal having corrosion resistance such as stainless steel, or a fabric such as Gore-Tex, but is not limited thereto.

FIGS. 6 and 7 illustrate that the heater 140 is positioned outside the cigarette 200, but the position of the cigarette 200 is not limited thereto. For example, the heater 140 may include a tubular heating element, a plate-type heating element, a needle-type heating element, or a rod-type heating element and may heat the inside or the outside of the cigarette 200 according to the shape of a heating element.

In addition, the aerosol generation device 100 may have a plurality of heaters 140. In this case, the plurality of heaters 140 may be positioned to be inserted into the cigarette 200 or may be positioned outside the cigarette 200. In addition, some of the plurality of heaters 140 may be positioned to be inserted into the cigarette 200, and others may be positioned outside the cigarette 200. In addition, the shape of the heater 140 is not limited to the shape illustrated in FIGS. 6 and 7 and may vary.

The vaporizer 130 may generate aerosol by heating the liquid composition, and the generated aerosol may be delivered to the user through the cigarette 200. In other words, the aerosol generated by the vaporizer 130 may move along the airflow path of the aerosol generation device 100, and the airflow path may be configured to allow the aerosol generated by the vaporizer 130 to be delivered to the user through the cigarette.

For example, the vaporizer 130 may include a liquid storage, a liquid delivery element, and a heating element, but is not limited thereto. For example, the liquid storage, the liquid delivery element, and the heating element may be provided as independent modules in the aerosol generation device 100.

The liquid storage may store liquid composition. For example, the liquid composition may be a liquid including a tobacco containing material having a volatile tobacco fragrance component, or a liquid including a non-tobacco component. The liquid storage may be fabricated to be detachable/attachable from the vaporizer 130 or may be fabricated integrally with the vaporizer 130.

For example, the liquid composition may include water, solvents, ethanol, plant extracts, flavors, flavoring agents, or vitamin mixtures. Flavors may include, but are not limited to, menthol, peppermint, spearmint oil, various fruit flavor components, and the like. Flavoring agents may include components that provide a variety of flavors or savors to the user. Vitamin mixtures may be a mixture of at least one of vitamin A, vitamin B, vitamin C and vitamin E, but are not limited thereto. The liquid composition may also include an aerosol forming agent such as glycerin and propylene glycol.

The liquid delivery element may deliver the liquid composition of the liquid storage to the heating element. For example, the liquid delivery element may be a wick such as cotton fiber, ceramic fiber, glass fiber, or porous ceramic, but is not limited thereto.

The heating element is an element for heating the liquid composition delivered by the liquid delivery element. For example, the heating element may be a metal heating wire, a metal hot plate, a ceramic heater, or the like, but is not limited thereto. In addition, the heating element may include a conductive filament such as nichrome wire and may be positioned as being wound around the liquid delivery element. The heating element may be heated by a current supply and may transfer heat to the liquid composition in contact with the heating element, thereby heating the liquid composition. As a result, aerosol may be generated.

For example, the vaporizer 130 may be referred to as a cartomizer or an atomizer but is not limited thereto.

The aerosol generation device 100 may further include general components in addition to the battery 110, the controller 120, and the heater 140. For example, the aerosol generation device 100 may include a display capable of outputting visual information and/or a motor for outputting tactile information. In addition, the aerosol generation device 100 may include at least one sensor (a puff sensor, a temperature sensor, a cigarette insertion sensor, etc.). In addition, the aerosol generation device 100 may be manufactured in such a structure in which external air may be introduced or internal gas may flow out even when the cigarette 200 is inserted.

Although not illustrated in FIGS. 6 and 7, the aerosol generation device 100 may be configured with separate cradles to form a system. For example, a cradle may be used for charging the battery 110 of the aerosol generation device 100. In some exemplary embodiments, the heater 140 may be heated while the cradle and the aerosol generation device 100 are coupled.

The cigarette 200 may be similar to a general combustion-type cigarette. For example, the cigarette 200 may be divided into a first portion including an aerosol-generating material and a second portion including a filter or the like. In some exemplary embodiments, the second portion of the cigarette 200 may also be provided with an aerosol-generating material. For example, an aerosol-generating material made in the form of granules or capsules may be inserted into the second portion.

The first portion may be completely inserted into the aerosol generation device 100, and the second portion may be exposed to the outside. In some exemplary embodiments, only a portion of the first portion may be inserted into the aerosol generation device 100, or a portion of the first portion and a portion of the second portion may be inserted thereinto. The user may puff aerosol while holding the second portion by the mouth of the user. In this case, the aerosol is generated by the external air passing through the first portion, and the generated aerosol passes through the second portion and is delivered to the user's mouth.

As an example, the external air may be introduced through at least one airflow inlet 150 formed in the aerosol generation device 100. For example, the opening and closing of the airflow inlet 150 formed in the aerosol generation device 100 and/or the size of the airflow inlet 150 may be controlled by a user. Accordingly, the amount of smoke and a smoking impression may be adjusted by the user. As another example, external air may be introduced into the cigarette 200 through at least one hole formed in the surface of the cigarette 200.

Hereinafter, an example of a cigarette 200 will be described with reference to FIG. 8.

Figure 8:
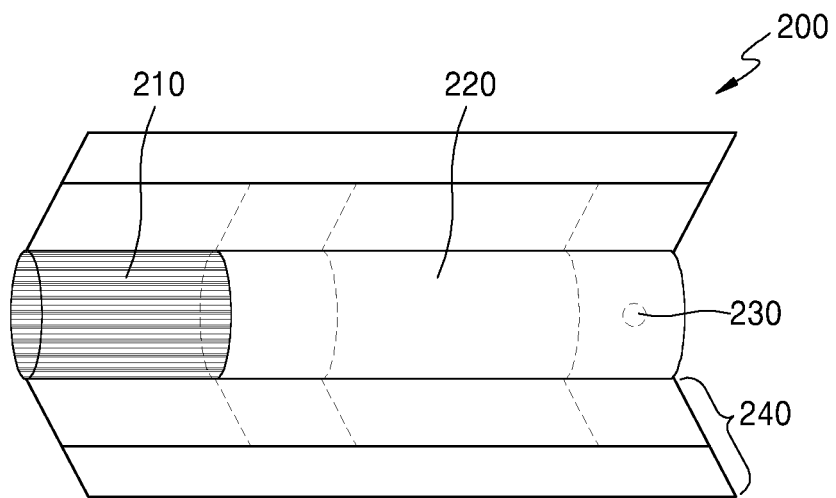
FIG. 8 illustrates a cigarette according to an exemplary embodiment.

FIG. 8 is a drawing illustrating an example of the cigarette 200.

Referring to FIG. 8, the cigarette 200 includes a cigarette rod 210 and a filter rod 220. The first portion described above with reference to FIGS. 6 and 7 includes the cigarette rod 210 and the second portion includes the filter rod 220.

In FIG. 8, the filter rod 220 is illustrated as a single segment but is not limited thereto. In other words, the filter rod 220 may include a plurality of segments. For example, the filter rod 220 may include a first segment for cooling the aerosol and a second segment for filtering a certain component provided in the aerosol. In addition, if needed, the filter rod 220 may further include at least one segment for performing another function.

The cigarette 200 may be packaged by at least one wrapper 240. The wrapper 240 may have at least one hole through which external air is introduced or internal gas is discharged. As an example, the cigarette 200 may be packaged by one wrapper 240. Alternatively, the cigarette 200 may be packaged by two or more wrappers 240 which overlap each other. For example, the cigarette rod 210 may be packaged by the first wrapper, and the filter rod 220 may be packaged by the second wrapper. In addition, the cigarette rod 210 and the filter rod 220, which are each packaged by a separate wrapper, may be coupled, and the cigarette 200 may be completely repackaged by a third wrapper. When each of the cigarette rod 210 and the filter rod 220 includes a plurality of segments, each segment may be packaged by a separate wrapper. Then, the cigarette 200, in which the segments packaged by the separate wrappers are coupled, may be entirely repackaged by another wrapper.

The cigarette rod 210 may include an aerosol-generating material. For example, the aerosol-generating material may include at least one of glycerin, propylene glycol, ethylene glycol, dipropylene glycol, diethylene glycol, triethylene glycol, tetraethylene glycol, and oleyl alcohol, but is not limited thereto. In addition, the cigarette rod 210 may contain other additives such as flavors, wetting agents, and/or organic acids. In addition, a fragrance liquid such as menthol or a moisturizer may be added to the cigarette rod 210 by being sprayed onto the cigarette rod 210.

The cigarette rod 210 may be manufactured in various ways. For example, the cigarette rod 210 may be manufactured in a sheet or a strand. In addition, the cigarette rod 210 may be manufactured as sheath obtained by cutting the tobacco sheet in small sizes. In addition, the cigarette rod 210 may be surrounded by a heat-conducting material. For example, the heat-conducting material may be, but is not limited to, a metal foil such as aluminum foil. For example, the heat-conducting material surrounding the cigarette rod 210 may evenly distribute the heat transferred to the cigarette rod 210 to improve the thermal conductivity applied to the cigarette rod 210, thereby improving the flavor of the cigarette. In addition, the heat-conducting material surrounding the cigarette rod 210 may function as a susceptor heated by an induction-heating heater. In this case, although not illustrated in the drawing, the cigarette rod 210 may further include an additional susceptor in addition to the heat-conducting material surrounding the outside thereof.

The filter rod 220 may be a cellulose acetate filter. The shape of the filter rod 220 is not limited to a particular shape. For example, the filter rod 220 may be a cylindrical type rod, or may be a tube type rod having a hollow therein. In addition, the filter rod 220 may be a recess type rod. When the filter rod 220 includes a plurality of segments, at least one of the segments may be manufactured in a different shape.

The filter rod 220 may generate flavor. As one example, a fragrance liquid may be sprayed into the filter rod 220, or a separate fiber coated with a fragrance liquid may be inserted into the filter rod 220.

In addition, the filter rod 220 may be provided with at least one capsule 230. Herein, the capsule 230 may perform the function of generating a flavor, or may perform the function of generating aerosol. For example, the capsule 230 may have the structure of fragrance-containing liquid packaged with a coating film. The capsule 230 may have a spherical or cylindrical shape, but the shape thereof is not limited thereto.

When the filter rod 220 includes a segment for cooling the aerosol, the cooling segment may include a polymer material or a biodegradable polymer material. For example, the cooling segment may include pure polylactic acid alone, but the material for forming the cooling segment is not limited thereto. In some exemplary embodiments, the cooling segment may include a cellulose acetate filter having a plurality of holes. However, the cooling segment is not limited to the above-described example and is not limited as long as the cooling segment cools the aerosol.

Meanwhile, although not illustrated in FIG. 8, the cigarette 200 may further include a front end filter. The front end filter may be located on one side of the cigarette rod 210 opposite to the filter rod 220. The front end filter may prevent the cigarette rod 210 from being separated and prevent the aerosol liquefied from the cigarette rod 210 from flowing into the aerosol generation device (100 of FIGS. 6 and 7) during smoking.

When the path through which the liquid composition flows in a vaporizer is not tightly sealed, the liquid composition may flow into other components in the aerosol generation device or outside the aerosol generation device.

When the leakage of liquid occurs repeatedly, components of the aerosol generation device may be contaminated and the performance thereof may deteriorate, and the aerosol generation device may not operate. In addition, when the liquid composition is leaked to the airflow inlet of the aerosol generation device, the leaked liquid composition may make the user of the aerosol to feel unpleasant.

The vaporizer according to the exemplary embodiments has a structure to prevent the leakage of the liquid composition. Accordingly, the leakage of the liquid composition to the outside of the vaporizer may be prevented. As the leakage of liquid is prevented, the above-described problems that may occur due to the leakage of liquid may also be resolved, thereby providing convenience to the aerosol generation device and a user using the aerosol generation device.

An aerosol generation device according to another exemplary embodiment further includes a water-repellent coating, which has been treated as being water-repellent, on an airflow inlet to prevent the leakage of the liquid composition through the airflow inlet, and at the same time, to prevent the external air from entering the aerosol generation device through the airflow inlet. In some exemplary embodiments, by controlling the amount of external air introduced into the aerosol generation device, the water-repellent coating may allow a vaporizer to generate high-quality aerosol.

Those of ordinary skill in the art related to the present exemplary embodiments may understand that various changes in form and details may be made therein without departing from the scope of the characteristics described above. The disclosed methods should be considered in descriptive sense only and not for purposes of limitation. Therefore, the scope of the disclosure is defined not by the detailed description of the disclosure but by the appended claims, and all differences within the scope will be construed as being included in the present disclosure.

What is claimed is:

1. A vaporizer comprising:
   a liquid storage for storing liquid composition;
   an upper cap portion coupled with the liquid storage and having a cavity for introducing the liquid composition of the liquid storage;
   a lower cap portion coupled with the upper cap portion to form an aerosol-generating space;
   a liquid delivery element positioned in the aerosol-generating space between the upper cap portion and the lower cap portion, and configured to absorb the liquid composition transferred from the liquid storage;
   a sealing portion having a coupling recess supporting at least one of end portions of the liquid delivery element, positioned between the upper cap portion and the lower cap portion, connected to the cavity, and configured to deliver the liquid composition from the liquid storage to the at least one of the end portions of the liquid delivery element;
   a heating element configured to heat the liquid delivery element to generate aerosol; and
   a leg portion extending from the upper cap portion to the lower cap portion, contacting at least a portion of the liquid delivery element, and configured to block a coupled portion between the coupling recess of the sealing portion and the at least one of the end portions of the liquid delivery element to block a flow of the liquid composition from the sealing portion to the aerosol-generating space.

2. The vaporizer of claim 1, wherein
   a top end of the coupling recess facing the upper cap portion is open.

3. The vaporizer of claim 1, wherein
   the sealing portion is coupled with the lower cap portion and positioned on facing sides of the lower cap portion to support each of the end portions of the liquid delivery element, extending from the facing sides of the lower cap portion to a center of the lower cap portion.

4. The vaporizer of claim 1, wherein
   the liquid delivery element is cylindrical, and the leg portion extends along at least a portion of an outer circumferential surface of the liquid delivery element, thereby surrounding the at least a portion of the outer circumferential surface of the liquid delivery element.

5. The vaporizer of claim 1, wherein
the coupling recess surrounds the at least one of end portions of the liquid delivery element.

6. The vaporizer of claim 1, wherein
the sealing portion further comprise an upper opening connected to the cavity, and a storage space for storing the liquid composition delivered from the upper opening and transferring, via connection to the coupling recess, the liquid composition to the at least one of end portions of the liquid delivery element inserted through the coupling recess.

7. The vaporizer of claim 1, further comprising
a liquid composition-absorbing member positioned between the liquid storage and the upper cap portion or between the upper cap portion and the sealing portion, and configured to delay the flow of the liquid composition absorbed by the liquid delivery element.

8. The vaporizer of claim 1, wherein
the upper cap portion, the lower cap portion, and the sealing portion comprise an elastic material.

9. The vaporizer of claim 1, wherein
the heating element has a coil- or filament-shape, and comprises at least one of nichrome, cantal, tantalum, stainless, tungsten, nickel and titanium.

10. The vaporizer of claim 1, wherein
the liquid delivery element comprises at least one of cotton, silica wick, stainless steel mesh, and fiberglass.

11. An aerosol generation device comprising:
an airflow inlet;
the vaporizer according to claim 1 for generating aerosol by heating external air introduced through the airflow inlet; and
an air-flow path through which the aerosol is discharged.

12. The aerosol generation device of claim 11, further comprising a water-repellent coating at the airflow inlet, wherein the water-repellent coating is processed to be water-repellent.

13. The aerosol generation device of claim 12, wherein the water-repellent coating has a mesh shape.

* * * * *